United States Patent [19]

Schittenhelm

[11] 4,260,895

[45] Apr. 7, 1981

[54] RADIATION DIAGNOSTIC APPARATUS FOR GENERATING TOMOGRAPHIC IMAGES

[75] Inventor: Rudolf Schittenhelm, Erlangen, Fed. Rep. of Germany

[73] Assignee: Siemens Aktiengesellschaft, Berlin & Munich, Fed. Rep. of Germany

[21] Appl. No.: 50,870

[22] Filed: Jun. 21, 1979

[30] Foreign Application Priority Data

Jul. 14, 1978 [DE] Fed. Rep. of Germany ....... 2831038

[51] Int. Cl.³ ................................................ A61B 6/00
[52] U.S. Cl. ................................................ 250/445 T
[58] Field of Search ..................................... 250/445 T

[56] References Cited

U.S. PATENT DOCUMENTS

| 3,971,948 | 7/1976 | Pfeiler et al. ...................... 250/445 T |
| 4,035,647 | 7/1977 | Hounsfield et al. ............. 250/445 T |
| 4,065,397 | 12/1976 | Ruhrnschopf .................... 250/445 T |
| 4,149,081 | 4/1979 | Seppi ................................ 250/445 T |
| 4,160,167 | 7/1979 | Weiss et al. ...................... 250/445 T |

*Primary Examiner*—Alfred E. Smith
*Assistant Examiner*—T. N. Grigsby
*Attorney, Agent, or Firm*—Hill, Van Santen, Steadman, Chiara & Simpson

[57] ABSTRACT

In an exemplary embodiment, a radiation source emits a radiation beam for penetrating the layer to be examined from different directions. A radiation receiver supplies electric output signals corresponding to the transmitted radiation intensity. A computer calculates the attenuation values of specific image points of the irradiated body layer based on the output signals. Correction devices are provided in the radiation receiver with which the radiation quality (mean energy) of the radiation striking the device is determined; each correction device preferably consists of a plurality of detectors arranged behind one another in the direction of the radiation, which detectors can be separated from one another by means of absorber layers. The output signals of the correction detectors serve for determining a correction for the radiation hardening in the patient.

3 Claims, 3 Drawing Figures

RADIATION DIAGNOSTIC APPARATUS FOR GENERATING TOMOGRAPHIC IMAGES

BACKGROUND OF THE INVENTION

The invention relates to a radiation diagnostic apparatus for generating tomographic images of an exposure subject with a positioning means for positioning the subject with a measuring arrangement for the irradiation of the exposure subject from different directions consisting of a radiation source which emits a radiation beam penetrating the layer to be examined, the dimension of said radiation beam perpendicular to the layer plane being substantially equal to the layer thickness and of a radiation receiver which supplies electric output signals corresponding to the measured radiation intensity and with a computer connected to the radiation receiver for calculating the attenuation values of specific image points of the irradiated body layer from the output signals of the radiation receiver.

In known radiation diagnostic apparatus of this type, socalled computer tomographs, x-ray tubes are provided as the radiation sources, which x-ray tubes emit a bremsstrahlung spectrum whose center of energy is displaced toward higher radiation energies by means of the self-absorption of the x-ray tube wall and by means of filters which serve for reducing the exposure of the patient to radiation. Nevertheless, in practice, the spectral distribution is still so wide that, upon the irradiation of the patient, a further radiation hardening ensues which depends on the thickness and on the composition of the irradiated subject. For the production of an image from the output signals of the radiation receiver, this varying radiation hardening within the patient has as a consequence that

- a correction according to this radiation hardening must be made for the sake of uniformity of the image and, above all, for a quantitative image evaluation;
- varying energy dependency of the beam detectors must either be avoided or likewise be corrected;
- fluctuations of the mean energy of the spectrum emitted from the radiator (including the filtering means associated with the x-ray source) must either be held sufficiently small or be likewise corrected.

SUMMARY OF THE INVENTION

The object of the invention is to design a radiation diagnostic apparatus of the type initially cited such that the beam quality can be measured within the beam receiver or in its immediate proximity, so that the described corrections can be precisely undertaken.

This object is inventively achieved in that detectors are provided in the beam receiver, with absorbers for the radiation connected in front of said detectors so that the mean radiation energy of the received radiation can be determined from the output signals of these detectors. The output signals of these detectors depend on the quality of the respectively received radiation so that this quality can be determined from them. They can therefore be employed for the correction of the measuring signals.

A radiation diagnostic apparatus of the type initially described is already known from the German O.S. 24 58 225 in which a correction of the type described above ensues; however, in this known radiation diagnostic apparatus, this correction is effected by means of a function stage in which the correction function is stored. The respective radiation quality is not measured.

According to an advantageous further development of the invention, the detectors can be arranged behind one another in the radiation direction and be separated from one another by means of absorber layers which attenuate the received radiation. However, it is also possible to arrange a plurality of detectors serving for the determination of the radiation quality in a row and to provide an absorber in front of each of these detectors. In this case, the absorbers of the individual detectors must exhibit different absorption for the received radiation.

Details of the invention derive from the sub-claims.

In the following, the invention is described in greater detail on the basis of the accompanying sheet of drawing; and other objects, features and advantages will be apparent from this detailed disclosure and from the appended claims.

DETAILED DESCRIPTION

Figure 1:
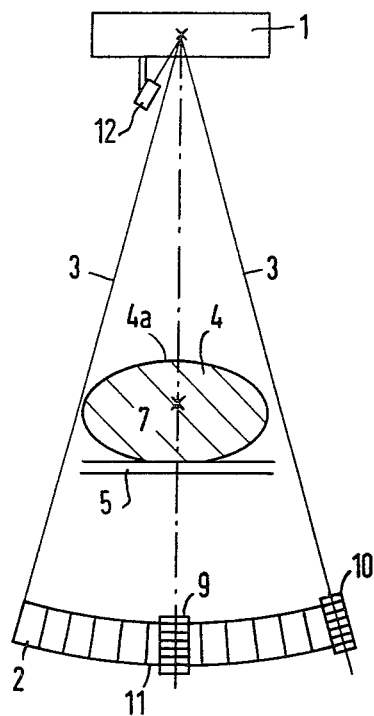
FIGS. 1 and 2 illustrate diagrammatically a radiation diagnostic apparatus according to the invention in front and side views.

FIG. 1 illustrates an x-ray tube 1 as a radiation source which, together with a radiation receiver 2, forms a measuring arrangement. This x-ray tube 1 emits a fan-shaped x-ray beam 3 whose spread in the cross sectional layer 4a to be examined of a patient 4 who is lying on a positioning couch 5 is so great that the entire layer 4a to be examined is permeated by x-radiation. The spread of the x-ray beam 3 perpendicular to the layer 4a is substantially equal to the thickness of the layer.

The radiation receiver 2 consists of a series of individual detectors, for example, of 256 detectors, of which each supplies a signal which corresponds to the intensity of the received x-radiation. The detectors of the radiation receiver 2 are connected to a computer 6 which calculates the attentuation values of specific image points of the layer 4a and, thus, calculates one image of the irradiated layer 4a of the patient 4 from the output signals of the detectors of the radiation receiver 2, which signals are formed during the rotation of the measuring arrangement 1, 2 through an angle of 360° about the rotational axis 7. This image is reproduced on a visual display 8. In order to reduce the patient's exposure to radiation the x-ray tube 1 can be pulsed during a scanning process so that, for example, one set of output signals of the radiation receiver 2 is generated per angular degree. In the example, 360×256 output signals are generated in this manner.

Figure 2:
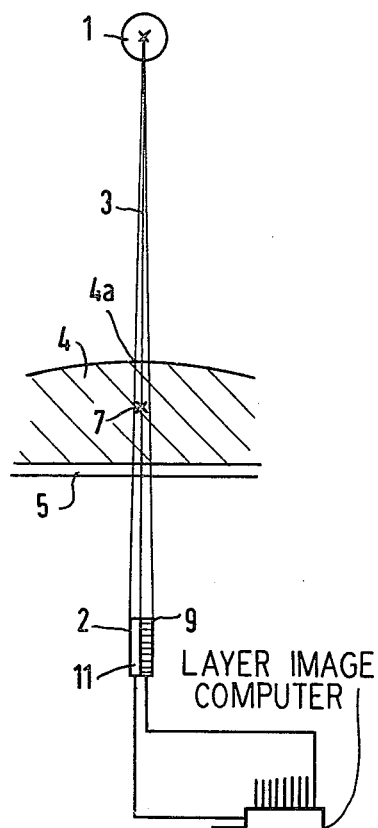

In order to determine the radiation hardening in the patient 4, two correction receivers 9 and 10 are provided in the example. A detector 11 of the radiation receiver 2 is illustrated in FIG. 2. The correction receiver 9 lies laterally next to this detector 11. According to FIG. 3, the correction receiver 9 consists of individual detectors 9a through 9n which lie behind one another as seen in the beam direction and are separated from one another by means of absorber layers 9o through 9z. The absorber layers 9o through 9z attenuate the received radiation as a function of the radiation quality and, thus, also of the hardening of the radiation in the patient 4. The output signals of the detectors 9a through 9n, thus, are a measure for the energy distribution in the primary spectrum and, upon introduction of the patient, also for the radiation hardening in the patient 4. They are supplied to the computer 6 for the determination and execution of the correction. In the same manner, the output signals of the correction receiver 10, which likewise consists of individual detectors separated from one another by means of absorber layers, are supplied to the computer 6 for a hardening correction of the signals supplied from the detectors of the radiation receiver 2.

In the example, two correction receivers 9 and 10 are provided which are distributed over the radiation receiver 2 in such manner that, given extant medical objects, they allow of statements concerning the spectrum over the entire width of the radiation receiver 2 which are sufficient for all practical purposes.

For examining the mean energy of the radiation emitted by the x-ray tube 1, a measuring probe 12 is provided which is placed at the outer edge of the x-ray beam 3 and constantly registers the radiation not influenced by the absorption in a patient or patient support 5.

Figure 3:
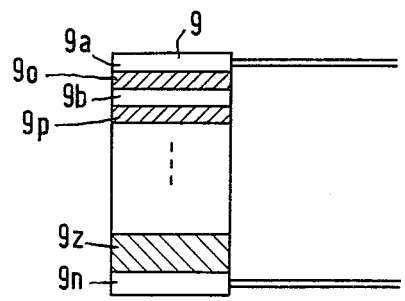
FIG. 3 shows a detail of the radiation receiver for the radiation diagnostic apparatus according to FIGS. 1 and 2.

In a variation of the example according to FIGS. 1 and 2, it is conceivable to replace one or more detectors of the radiation receiver 2 by means of correction receivers according to FIG. 3. In this case, the signal required for the image reconstruction can be gained by means of a summing of the output signals of the individual detectors of a correction receiver. The correction factors for the energy displacement of the x-radiation can be formed from the differences of the signals of the individual detectors 9a through 9n, FIG. 3.

The absorber layers 9o through 9z can be omitted when the hardening effect in the individual detectors of a correction receiver itself is sufficient for a sufficient recognition of energy differences in the input spectrum. In this case, the absorber disposed in front of an individual detector is formed by the preceding individual detector.

For the correction, i.e. for measuring the mean energy of the received radiation, it is also conceivable to arrange a plurality of correction detectors lying next to one another in a row laterally adjacent to the row of detectors 11 of radiation receiver 2 and to lay an individual absorber of a respective different attenuation in front of each respective correction detector.

In the example of FIGS. 1 and 2, the spread of the x-ray beam 3 as viewed in FIG. 2 slightly exceeds the layer thickness to be examined by detectors 11 of the radiation receiver 2, so that the correction receivers 9, 10 are impinged by a suitable sample of the beam; in the arrangement of FIG. 1 only the central part of a fan shaped beam 3 need have a depth exceeding the thickness of the layer to be examined since the receiver 10 can be beyond and in line with the row of detectors 11. Where detector 10 is arranged laterally next to a detector 11 as shown for detector 9 in FIG. 2, the beam may also have greater depth at the margin of the beam which is directed toward detector 10, this margin being directed to one side of body 4 for all angular positions of source 1 and receiver 2 relative to the body. Thus, the irradiated layer is slightly thicker than the layer which is imaged at least at the central portion of the beam, for the embodiment specifically shown in FIGS. 1 and 2.

It will be apparent that many modifications and variations may be effected without departing from the scope of the novel concepts and teachings of the present invention.

I claim as my invention:

1. Radiation diagnostic apparatus for the generation of tomographic images of an exposure subject with a positioning means for an exposure subject; with a measuring arrangement for the irradiation of the exposure subject from different directions; the measuring arrangement comprising a radiation source which emits a radiation beam penetrating the layer to be examined, the dimension of said beam perpendicular to the layer plane being substantially equal to the layer thickness, and a radiation receiver which supplies electric output signals corresponding to the measured radiation intensity, and a computer connected to the radiation receiver for the calculation of the attenuation values of specific image points of the irradiated body layer from the output signals of the radiation receiver; characterized in that detectors (9b through 9n) are provided in the radiation receiver (2), and in that absorber means (9o through 9z) is located in said radiation receiver and is located with said radiation receiver on the side of the positioning means (5) opposite the radiation source (1) so as to intercept the radiation beam from said source after penetration by said beam of the layer to be examined, said detectors (9b through 9n) being disposed for sensing beam intensity after passage of the beam through said absorber means (9o through 9z) so that the radiation hardening of the received radiation can be determined from the output signals of these detectors (9b through 9n).

2. Radiation diagnostic apparatus according to claim 1, characterized in that the detectors (9b through 9n) are arranged behind one another in the direction of the radiation, the absorber means comprising absorber layers (9p through 9z), which attenuate the received radiation, separating the successive detectors.

3. Radiation diagnostic apparatus according to claim 1, characterized in that the detectors (9b through 9n) lying behind one another are arranged laterally next to a measuring detector (11).

* * * * *